United States Patent [19]
Harats et al.

[11] Patent Number: 5,747,340
[45] Date of Patent: May 5, 1998

[54] TARGETED GENE EXPRESSION USING PREPROENDOTHELIN-1 PROMOTERS

[75] Inventors: Dror Harats, Ramat-Gan, Israel; Hiroki Kurihara, Toyko, Japan; Paula Nanette Belloni, Moss Beach; Charles Elliott Sigal, San Francisco, both of Calif.

[73] Assignee: Syntex (U.S.A.) Inc., Palo Alto, Calif.

[21] Appl. No.: 395,742

[22] Filed: Feb. 28, 1995

Related U.S. Application Data

[63] Continuation-in-part of Ser. No. 254,015, Jun. 3, 1994, abandoned.

[51] Int. Cl.$^6$ .............................. C12N 5/00; C12N 15/00; C07H 21/04
[52] U.S. Cl. .................. 435/375; 435/172.3; 435/320.1; 514/44; 536/24.1; 935/6; 935/34; 935/22
[58] Field of Search ..................... 544/14; 435/320.1, 435/172.3, 375; 536/24.1; 935/36, 6, 62, 34, 22

[56] References Cited

U.S. PATENT DOCUMENTS 5,288,846  2/1994  Quertermous et al. .............. 435/172.3

OTHER PUBLICATIONS

Hilkert, et al., "Transgene Expression Directed By The Endothelin–1 Promoter Is Cell–Type–Specific But Integration–Site–Dependent", J. Vas. Med. & Biol., vol. 4, No. 2–3 (138–147) Apr./Jun. 1993.
Lee, et al., "Expression Of The Potent Vasoconstrictor Endothelin In The Human Central Nervous System", J. Clin. Invest., vol. 86, Jul. 1990, 141–147.
Bloch, et al. "Structural Organization And Chromosomal Assignment Of The Gene Encoding Endothelin", J. Biol. Chem., vol. 264, No. 18, 10851–10857, 1989.
Inoue, et al., "The Human Endothelin Family: Three Structurally And Pharmacologically Distinct Isopeptides Predicted By Three Separate Genes", Proc. Natl. Acad. Sci., vol. 86, 2863–2867, Apr. 1989.
Lee, et al., "Functional Analysis Of The Endothelin–1 Gene Promoter", J. Biol. Chem., vol. 265, No. 18, 10446–10450, Jun. 25, 1990.
Wilson, et al., "A Nonerythroid Gata–Binding Protein Is Required For the Function of The Human Preproendothelin–1 Promoter In Endothelial Cells", Mol. Cell. Biol., Sep. 1990, 4854–4862, vol. 10, No. 9.
Yanagisawa, et al., "A Novel Potent Vasoconstrictor Peptide Produced By Vascular Endothelial Cells", Nature, vol. 332, 31, Mar. 1988, 411–415.
Inoue, et al., "The Human Preproendothelin–1 Gene", J. Biol. Chem., vol. 264, No. 25, Sep. 5, 1989, 14954–14959.
Miller et al (1995) FASEB J 9: 190–199.
Culver et al (1994) Trends in Genetics 10: 174–178.
Hodgson (1995) Exp Opin Ther Patents 5: 459–468.
Marshall (1995) Science 269: 1050–1055.
Brinster et al (1988) Proc Natl Acad Sci USA 85: 836–840.

*Primary Examiner*—Bruce R. Campbell
*Attorney, Agent, or Firm*—Heller Ehrman White & McAuliffe

[57] ABSTRACT

This invention provides a vector for expression of a nucleic acid cassette in bronchial epithelial and vascular endothelial cells comprising a segment of the 5'-flanking region of the preproendothelin-1 gene, upstream from the transcription start site, the first exon of the preproendothelin-1 gene, and a nucleic acid cassette, wherein the nucleic acid cassette is located within the first exon, in sequential and positional relationship for expression of the nucleic acid cassette.

15 Claims, 8 Drawing Sheets

```
m  GTGTGTGTGTGTGTGTGTGTGTGTGTGTGTGTGTGTGTGTAGTTCTTCGATCGGATAC---TAGGGAGAT  -695
                                                            ||| ||||||||
h  TT-CAATCAGTTTATCAGCCCTCCTCCCAGGGAATGTGACACACAA)AGAACTTATCGGGGCTTCATCAG-TGAT  -675 m  AAGGATGTACTTGACA-AAACCACATGTTGTTGTTATCATTATTAGTTTCCTTCCTGCTAACTCCTGACGA  -616
      ||||  || || |      ||||||||  |||| || || |||||  |||||    |   ||| |
h  AGGGAAAAGACTGGCATGGCCTAAAACG-AGCTCTGAT-GTTATT--TTTAAGCTCCCTTCTTGCCAATCCCTCACGG--  -599 m  ATCTTTCTCACCTCAAATGCGAAGTACTTAGTTTAGAAAGACTTGGTGGAA--GGGGTGTGTGGAAAAGTAGGGTG  -538
   |||| | |        |||||      | ||  |||| | |     ||         ||| |||| ||| ||
h  ATCTTTCTC-CGATAGATGCAAAGAACTTCAG--CAAAAAAGACCCGCAGGAAGGGGGCTTGAAG-AGAAAAGTACGTTG  -524 m  ATCTTCAAACTAATCTGTTCCCCGCCCCAGTAGCTCGGATTCAAGAGCGAAGAGTGGGATCGTCCCTTGTT  -459
   |||||  |   |                      |||||||||||  || ||| |||||||  ||| |||
h  ATCTGCCAAAATAGTCCTG--------ACCCCCAGTAG-TGGG------CAGTGACGAG--GGAGAGCATTCCCTTGTT  -463 m  TG-------ATCAGAAAGACATAAAGGAAATCAGTGACAATGATCAGCCCCACCTTCCACCCCCCT  -392
   ||        ||  | |||||||||||||| ||| || || |||| |||  |||   ||| ||||
h  TGACTGAGACTAGAATGCGGAGAGACATAAAAGGAAATGAAGCGAGCAACAATTAAAAAAATTCC--CCGCACAC----  -390 m  GCGGCGGCACAATACAATCTATTT-AATTGTACTTCATTCTTTCATTCCAATGGGTGACTTGCTTTCTGGAG-AAAC  -315
   ||||||| || | ||| ||| ||  || |||||||        ||| | ||||  || ||||||||| ||||
h  -------AACAATACAATCTATTTAAACTCTGGGCTCATACTTTTCATACCAAATGTATGACTTTTTTCTGGAGTCCCC  -317 m  TCT---TGATTCTTGAACTCTCGGGGCTGCAGCTAGCAAAAGGGGAAGCGGGGCT------GCTGCTCCTTCTGCAGGTTCTGC  -243
   |||    || | ||||||||| ||||||||| |||| | | ||        ||       ||  ||| |||| || ||
h  TCTTCTGATTCTTGAACTCTCGAGGCTGGGCTGGGCTAGCAAA--GGGGAAGCGACTCCAGCAGCGG-GCAGGTTTAGC--  -239 m  AGGGGTCTCGTCAGTGGGTGTTTCTTTTTCTAGCCCTGGGAATTCAGAATGTCAGGCGTCGCCTCTGAA  -164
   ||| |||  ||       || ||||| ||| ||  ||||||||||||||||||||||||||||||||||
h  AAAGTC----TCTAATGGTATTTTCTTTTTCTTTAGCCCTGCCCCCCGAATTGTCAGAGACCGGTCGTCTGCTTCTGAA  -164
```

FIG. 2B

```
m GTTAGCCGTGATTTCCTCTAGAGCCCGGGTCTTATCTTGGCTGCAGTTGCCTGTGGNGACTAATCACACAATAACAT   -85
    ||||||||||||||||||||||||  |||||  ||| || ||||||||||||| ||||  ||||||||||||||
h GTTAGCAGTCGATTTCCTTTCGGGGCCTTGG--CTTATCTTGCCTGTGTGNGACTAATAACACAATAACAT         -86 m TGTTTAGGGCTGGAATAAAGTCAGAGCTGTTTACCCCCACTCT-ATACGGGTTCAATATATAAAGGCGGGAGAACTG   -7
    |||| ||||||||||||||||| |||||||||||||||||||| || |||||||||| || ||||  |||||||||
h TGTCTGGGGCTGGAATAAAGTCGAGAGCTGTTTACCCCCACTCTAATACTGGGTTCAATATATAAAGCCCGGCAGAGAGCTG  -7 m TCCGAGTCAGACGCGTTCCTGCACCGCGC---TGAGAGCCTGACCCGGTCC--GCTGTCCTTGCCTGCCTCC         +71
    ||||||||||||||||||  ||||| |||    |||||   || |||||||  |||||| ||||||| ||||
h TCCAAGTCAGACGCGCTCCTGCATCGCCTCTGCCCAGGCGAACGGGTCCTG---CGCCTCCTGCAGTCCTCCACCGCC    +71 m -CGGCTGCCCGC--GACGCT----TTCGC---CCCAGTGAAGGGC----CACTTGCTGAGGACCCGGCT---GAGATCTAAA   +137
    |||||  ||||  ||||||     |  |    ||||||||||        | ||||||||||    |||  ||||||||||
h GCGTGCGCAGCAGCGAGCGTTCCTCCTGCGTGCCCAGTGAAGGGCTGCAGGACTTGCTGAGGACCCGGCTAAAGGGCACTTGG   +150 m AAAAAACAAAAACAAAAACAAAAAACAAAAAACAAAAAACAAAAAAACCAGAGAGGGGGATCAGAGACCAGACACCG-TCCTCTTGTTTGCATTG   +215
   ||   || |  |                                    |||||||   || || || ||||  || ||||||| |||||  |||
h AAAAAACAAAAAA---------------------------------------CCAGAGAGGGCGATCAGAGAGCAGACACCGGTCCTCTTGTCTGCATTG  +229 m GCTGAAGGATCGCTTTGAGATCTGAGGAACCC--GCAGGCTTTGAGGACTGAAGCTGTTTCTTCGTTTCCTTTG
    |||||||||||||||||||||||||||||||   |||||||||||||||| |||||||||| |||||||||||
h GCTGAAGGATCGCTTTGAGATCTGAGGAACCC-GCAGGCTTTGAGGACTGAAGCTGTTTCTTCGTTTCCTTTG
```

Bgl II

```
m  AGTTCCATTTGCAACCGAGTTTCTTTTTCCTTTTTCCCACTCTCTGACCCCTTTGCAGAATGGATTATTTCCC  +294
      ||||  ||||  |||  ||| ||| |||||                ||||||||||||||||||| ||||
h  GGTTCAGTTTGAACGGGAGGTT--------TTTGATCCCTTT-----------TTTCAGAATGGATTATTTGCTC  +288 m  GTGATCTTCTCTGCTGTTGCTGTGACTTCCAAGGAGCTCCAGAAACAGgtaggcgccactgcgaacctttctactc  +373
   |||||||||||| ||||| ||||||| ||||||||||||||||||||  |||| ||||| ||||| | ||||| 
h  ATGATTTCTCTGCTGTGTTGCCTTGCCCAAGGAGAGCTCCAGAAACAGgtaggcacgctcgtcgttgactgacttccg  +367 m  agcgcagcagttatcgcttctgtcttctcccacttttcctcttccttt-tccttttttattcatttccttt  +451
          ||||||      ||| ||| |||| |||| |    |  |||    |   ||||| |||||||
h  gaattacacaagttagtg-tgttcctatatccac--cttcatgctcctttctgcttccttcattttccccgtcctttttatgactgc  +444 m  a--attactg---aagctccagcagca--agtgcctttacaattaattaacttcctgtgtgaagcgaaagaaataaaaccccc  +523
     | ||||||    |||||||||||||   ||||                |                   |||
h  agcttagagagcaagtgtcctg-agaattactg-ctgaaacgtaccttaagtcct---tctagtgtaaaatgtaaaattcc  +518 m  tgt--ttgaatacagctgactacaaccgagtatcgcatagcttc                                     +560
         ||||||||||     ||| ||||||||| ||||     
h  tctactgaatacaattagtgcaattgactgactataacatgacatt                                    +559
```

TARGETED GENE EXPRESSION USING PREPROENDOTHELIN-1 PROMOTERS

CROSS-REFERENCE TO RELATED APPLICATIONS

This application is a continuation-in-part of U.S. patent application Ser. No. 08/254,015, filed Jun. 3, 1994, abandoned, the disclosure of which is incorporated by reference herein.

FIELD OF THE INVENTION

This invention relates to tissue specific gene expression, in particular vectors for expressing polypeptides in bronchial epithelial and vascular endothelial cells.

BACKGROUND OF THE INVENTION

The potential of genetic therapy for ameliorating or reversing the ravages of countless human diseases is the subject of intensive research. Interest is focused in particular on those disorders which respond poorly to conventional therapies, such as cancer, genetic diseases, cardiovascular diseases, and immune disorders. Brain tumors, breast cancer, leukemia, lymphoma, melanoma, multiple myeloma, non-small cell lung cancer, renal carcinoma, cystic fibrosis, Gaucher disease, hypercholesterolemia, and AIDS are the subjects of various gene therapy protocols. In many approaches, cells are removed from a patient, genetically altered, and then reintroduced. Alternatively, a gene may be introduced in vivo into the individual in whom expression is desired. In this latter regimen, it is preferable that the gene either be delivered only to the target tissue or that expression of the gene be regulated to occur only in the target tissue. However, conventional drug delivery technology (oral, parenteral, iv) is not generally conducive to tissue specificity. Therefore, tissue specific expression systems, wherein the gene to be expressed is coupled with a regulatory element which induces expression preferentially in the target tissue, are desired.

The vascular endothelium plays a crucial role in a number of physiologic processes including coagulation and fibrinolysis, the regulation of vascular tone, and the mediation of local immune and inflammatory responses. Tissue specific gene expression in the vascular endothelium would provide a means for targeting genes capable of alleviating disease states involving this tissue, such as atherosclerosis, restenosis, and hypertension. In addition, tissue specific gene expression provides a mechanism for the creation of transgenic animals which either overexpress or inhibit selected proteins implicated in certain disease states.

Endothelin-1 is a 21 amino acid peptide originally characterized as a potent vasoconstrictor synthesized by endothelial cells. (Yanagisawa, et al., *Nature*, 332:411–415 (1988)). The expression of endothelin-1 in mammals is fairly specific for the endothelium, although there is some expression in other cells, mainly the airway and gastrointestinal epithelium, neurons, and glomerular mesangial cells. Endothelin-1 induces mitogenesis and increases the expression of protooncogenes in vascular smooth muscle cells, fibroblasts, aid glomerular mesangial cells. Other actions attributed to endothelin-1 include causing the release of atrial natriuretic factor from atrial cardiocytes in culture and inhibiting the release of renin from glomeruli. The effects of endothelin-1 on vascular smooth muscle cells implicate it in the pathogenesis of atherosclerosis and hypertension.

Endothelin-1 is derived from the prepropeptide preproendothelin-1 which has a promoter region with endothelial cell specificity as assessed by in vitro analysis. (Bloch, et al., *J. Biol. Chem.*, 264:0851–0857 (1989); Lee, et al., *J. Biol. Chem.*, 265:0446–0450 (1990); Wilson, et al., *Mol. Cell. Biol.*, 10:4854–4862 (1990); Lee, et al., *J. Bio. Chem.* 266:16188–16192 (1991)). The 5'-flanking region of preproendothelin-1 thus appears attractive for vascular endothelial tissue specific gene expression.

SUMMARY OF THE INVENTION

This invention provides a vector for expression of a nucleic acid cassette, preferably in bronchial epithelial and vascular endothelial cells. The vector for expression of a nucleic acid cassette comprises a segment of the 5'-flanking region of the preproendothelin-1 gene, upstream from the transcription start site, the first exon of the preproendothelin-1 gene, and a nucleic acid cassette, wherein the nucleic acid cassette is located within the first exon, in sequential and positional relationship for expression of the nucleic acid cassette. The nucleic acid cassette contains the nucleic acid required to express a desired product in the target tissue. The 5'-flanking region segment comprises about the first 0.45 kb upstream from the transcription start site, preferably about 1.4 kb, most preferably about 5.9 kb, up to about 9.1 kb.

In another embodiment there is provided a vector as described above also comprising the first intron, preferably about 0.8 kb of the first intron, of the preproendothelin-1 gene, located downstream of the nucleic acid cassette, in sequential and positional relationship for expression of the nucleic acid cassette.

In a third embodiment there is provided a vector made up of a segment of the 5'-flanking region of the preproendothelin-1 gene and the first exon wherein the coding and noncoding regions of the exon are separated at a Bgl II restriction site and the nucleic acid cassette is positioned between the noncoding and coding regions of the exon, downstream from the promoter, in sequential and positional relationship for expression of the nucleic acid cassette.

In a fourth embodiment there is provided a vector made up of a segment of the 5'-flanking region of the preproendothelin-1 gene, the first exon, and about 0.8 kb of the first intron of the preproendothelin-1 gene. The coding and noncoding regions of the exon are separated at a Bgl II restriction site and the nucleic acid cassette is positioned between the noncoding and coding regions of the exon, downstream from the promoter and upstream from the intron, in sequential and positional relationship for expression of the nucleic acid cassette.

The nucleic acid cassette comprises a nucleic acid sequence encoding a protein, a polypeptide, or an antisense RNA, preferably a recombinant human nucleic acid sequence.

Also provided is a method for introduction of a preproendothelin-1 vector into bronchial epithelial or vascular endothelial cells by the steps of cotransfecting the vector with a selectable marker and selecting the transformed cells.

Transgenic animals containing the preproendothelin-1 vector are also provided.

Another embodiment provides a method for the in vivo transduction of bronchial epithelial or vascular endothelial cells by complexing the preproendothelin-1 vector with a delivery vehicle and contacting the cells with the vector-vehicle complex for a time sufficient to transduce the cells. The delivery vehicle may be a liposome or a virus, preferably a cationic liposome.

The vector may further contain a moiety responsive to stimuli for controlling the expression of the product of the nucleic acid cassette.

Methods for treating atherosclerosis, restenosis, and hypertension by transfecting vascular endothelial cells and asthma and bronchitis by transfecting bronchial epithelial cells with a preproendothelin-1 vector expressing a gene which reverses or retards the progress of the disease are also provided.

Also provided is the isolated and purified genomic murine preproendothelin-1 promoter region.

DETAILED DESCRIPTION OF THE INVENTION

Definitions

As used herein the following terms have the meanings set forth below.

"Endothelial" refers to the layer of flat cells lining especially the blood and lymphatic vessels and the heart.

"Epithelial" refers to the cellular avascular layer covering the free surface of most tissues.

"Promoter" refers to the site of binding of DNA-dependent RNA polymerase.

"Transformed" refers to the process or mechanism of inducing changes in the characteristics (expressed phenotype) of a cell by the mechanism of gene transfer whereby DNA is introduced into a cell in a form such that the cell expresses a specific gene product of the DNA or alters expression of endogenous gene products.

"Transduction" and "transfection" refer to the processes of introducing a DNA expression vector into a cell.

"Nucleic acid cassette" refers to the genetic material of interest which can express a protein, polypeptide or RNA and which is capable of being incorporated into the bronchial epithelial or vascular endothelial cells. The nucleic acid cassette is positionally and sequentially oriented within the vector such that the nucleic acid in the cassette can be transcribed into RNA or antisense RNA and, when necessary, translated into proteins or polypeptides in the transformed cells.

A "vector" is a DNA molecule that autonomously replicates in a cell and to which another nucleic acid segment may be attached and itself replicated.

This invention provides a vector for expression of a nucleic acid cassette, preferably in bronchial epithelial and vascular endothelial cells. The vector for expression of a nucleic acid cassette comprises a segment of the 5'-flanking region of the preproendothelin-1 gene, upstream from the transcription start site, the first exon of the preproendothelin-1 gene, and a nucleic acid cassette, wherein the nucleic acid cassette is located within the first exon, in sequential and positional relationship for expression of the nucleic acid cassette. The nucleic acid cassette contains the nucleic acid required to express a desired product in the target tissue. The 5'-flanking region segment comprises about the first 0.45 kb upstream from the transcription start site, preferably about 1.4 kb, most preferably about 5.9 kb, up to about 9.1 kb.

In another embodiment there is provided a vector as described above also comprising the first intron, preferably about 0.8 kb of the first intron, of the preproendothelin-1 gene, located downstream of the nucleic acid cassette, in sequential and positional relationship for expression of the nucleic acid cassette.

In a third embodiment there is provided a vector made up of a segment of the 5'-flanking region of the preproendothelin-1 gene and the first exon wherein the coding and noncoding regions of the exon are separated at a Bgl II restriction site and the nucleic acid cassette is positioned between the noncoding and coding regions of the exon, downstream from the promoter, in sequential and positional relationship for expression of the nucleic acid cassette.

In a fourth embodiment there is provided a vector made up of a segment of the 5'-flanking region of the preproendothelin-1 gene, the first exon, and about 0.8 kb of the first intron of the preproendothelin-1 gene. The coding and noncoding regions of the exon are separated at a Bgl II restriction site and the nucleic acid cassette is positioned between the noncoding and coding regions of the exon, downstream from the promoter and upstream from the intron, in sequential and positional relationship for expression of the nucleic acid cassette.

The nucleic acid cassette comprises a nucleic acid sequence encoding a protein, a polypeptide, or an antisense RNA, preferably a recombinant human nucleic acid sequence.

Also provided is a method for introduction of a preproendothelin-1 vector into bronchial epithelial or vascular endothelial cells by the steps of cotransfecting the vector with a selectable marker and selecting the transformed cells.

Transgenic animals containing the preproendothelin-1 vector are also provided, particularly transgenic mice expressing the human 15-lipoxygenase gene.

Another embodiment provides a method for the in vivo transduction of bronchial epithelial or vascular endothelial cells by complexing the preproendothelin-1 vector with a delivery vehicle and contacting the cells with the vector-vehicle complex for a time sufficient to transduce the cells. The delivery vehicle may be a liposome or a virus, preferably a cationic liposome, such as DOTMA and related compounds, as described in U.S. Pat. No. 5,049,386, the disclosure of which is incorporated by reference herein.

The vector may further contain a moiety (gene switch) responsive to stimuli for controlling the expression of the product of the nucleic acid cassette.

Overexpression of select proteins permits in vivo evaluation of biological sequelae that have been suggested from in vitro data. Moreover, expression of peptide inhibitors, soluble receptors, anti-sense cDNA or other molecules that may not be bioavailable allows the elucidation of in vivo vascular biology that was previously difficult to assess. Furthermore, the ability to knockout function in a restricted fashion offers advantages over systemic approaches which affect a variety of systems and sometimes lead to lethal phenotypes. Finally as gene therapy becomes more feasible, it is clear that one of its limitations is the inability to direct expression to the desired cells. Both the endothelial cells and airway epithelial cells are important targets for gene therapy in disease such as atherosclerosis, restenosis, hypertension, asthma, bronchitis, and cystic fibrosis. The preproendothelin 5'-flanking sequence of this invention provides the ability to achieve expression of desired genes in these select somatic cells, thereby affording new opportunities for genetic therapy.

Various methods of transduction are possible, including microinjection, $CaPO_4$, lipofection, use of a gene gun, and DNA vector transport. The vector can be transduced into the cells in vitro by any of the variety of ways described above. The delivery of the vector in vivo may be accomplished by liposomal or viral complexes capable of non-covalent binding to DNA and transport of the DNA through the cell membrane. One method for ex vivo introduction of the vector into cells includes a cotransfection of the vector with a selectable marker. The selectable marker is used to select those cells which have become transformed. The transformed cells can then be used in any of the methods described in the present invention.

Another embodiment of the present invention is a method of making transgenic animals comprising the steps of inserting a vector of this invention into the embryo of an animal. The transgenic animal includes the animal into whose embryo the vector was inserted and any progeny thereof. The term progeny as used herein includes direct progeny of the transgenic animal as well as any progeny of succeeding progeny. Thus, one skilled in the art will readily recognize that if two different transgenic animals have been made using different genes in the nucleic acid cassette and they are mated, the possibility exists that some of the resulting progeny will contain two or more introduced sequences. One skilled in the art will readily recognize that by controlling the matings, transgenic animals with multiple vectors can be made.

In the transgenic animals that contain a human nucleic acid cassette in its germ and somatic cells, the nucleic acid cassette of the said vector is predominantly expressed in the bronchial epithelial and vascular endothelial cells. This is a distinct advantage over other transgenic animal models where there is not as much control over the expression of the sequence in the tissues.

A variety of proteins and polypeptides can be expressed in transformed cells by the sequence provided in the nucleic acid cassette. Exemplary proteins or polypeptides which can be expressed include cellular adhesion molecules, cytokines, hormones, growth factors, enzymes, clotting factors, apolipoproteins, receptors, drugs, inhibitors, antigens, and oncogenes. Specific examples of these compounds include cystic fibrosis transmembrane regulator (CFTR), granulocyte macrophage colony stimulating factor (GM-CSF), Heart/Lung Selective DNAse, the antisense oligonucleotide GEM 91, VCAM-1, ICAM-1, TNF-1 receptors, insulin-like growth factors, angiogenesis factor, acidic and basic fibroblast growth factors and angiogenin, and proteins from viral, bacterial and parasitic organisms which can be used to induce an immunologic response.

The vectors of this invention are useful for the tissue specific expression of genes for treatment of diseases affecting the cardiovascular and pulmonary systems, in particular for diseases involving the bronchial epithelium, such as asthma, bronchitis, lung cancer, emphysema, cystic fibrosis, pneumonia, and tuberculosis, and for the treatment of diseases affecting the vascular endothelium, such as atherosclerosis, restenosis, and hypertension. Generally inflammatory diseases involving endothelial cell activation should be susceptible to inhibition by genes delivered via the vectors of this invention. In addition, the lower, but still significant expression in the brain suggests utility for CNS disorders, including Alzheimer's and Parkinson's diseases.

The following examples are provided for illustrative purposes only and should not be construed to limit the invention in any manner.

Standard molecular biological procedures were employed as described in T. Maniatis, E. F. Fritsch, and J. Sambrook, Molecular Cloning: A Laboratory Manual, Cold Spring Harbor Laboratory, Cold Spring Harbor, N.Y. (2nd ed., 1989) and B. Hogan, F. Costantini, and E. Lacy, Manipulating the Mouse Embryo, Cold Spring Harbor Laboratory, Cold Spring Harbor, N.Y. (1986), the disclosures of which are incorporated by reference herein. Commercial sources for materials used in these examples are indicated where appropriate, recognizing that alternative materials and/or sources may equally well serve the purposes of this invention.

EXAMPLE 1

Cloning of the murine preproendothelin gene

To obtain genomic clones for the murine preproendothelin-1 (PPET-1) promoter region, oligonucleotide probes corresponding to the nucleotide sequence of the entire murine endothelin-1 (ET-1) coding sequence (K. Saida, et al., *J. Biol. Chem.* 264:4613–4616 (1989)) were used to screen a BALB/c mouse genomic library (Clontech Laboratories Inc. Palo Alto, Calif.) under high stringency conditions. DNA sequencing was performed using the dideoxy chain termination method. A fragment containing the 5'-flanking region of the PPET-1 gene was subcloned, and the transcription start-site was determined by primer extension.

Figure 1:
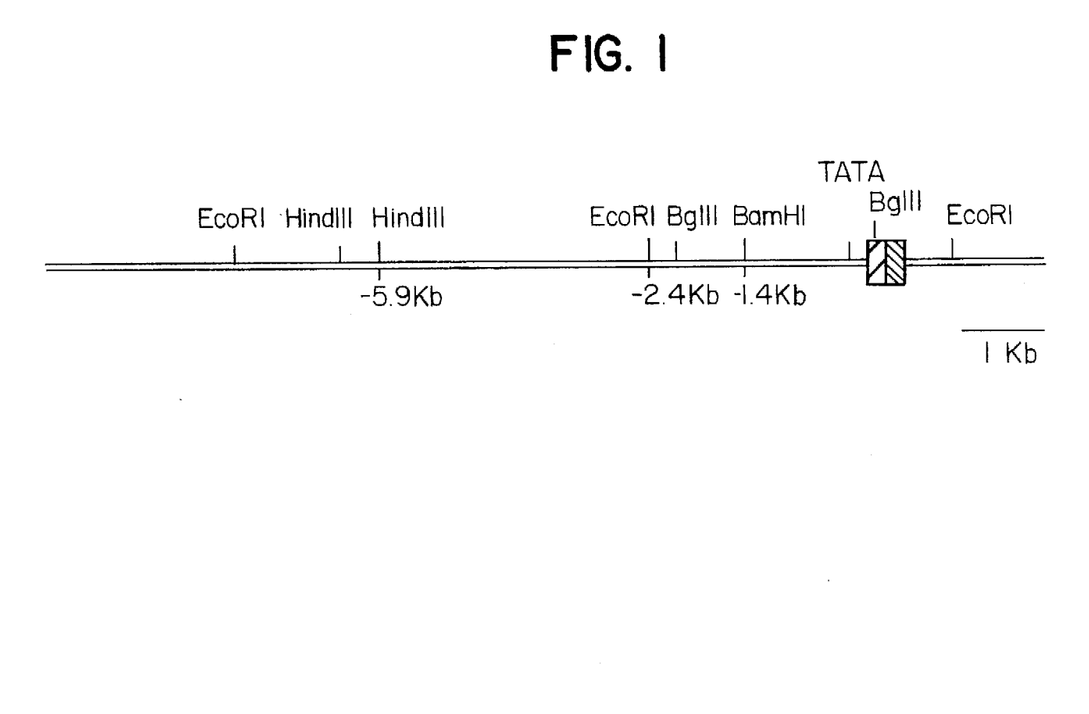
FIG. 1: Restriction map of the mouse preproendothelin-1 promoter region. The first exon contains the 5'-noncoding region (hatched) and the 5'-end of the coding region (shaded).

FIG. 1 sets forth a restriction map of the mouse preproendothelin-1 promoter region. The first exon contains the 5'-noncoding region (hatched) and the 5' end of the coding region (shaded). The Bgl II site in the first exon was used for subcloning. Location of the putative TATA box is also shown.

Figure 2A:
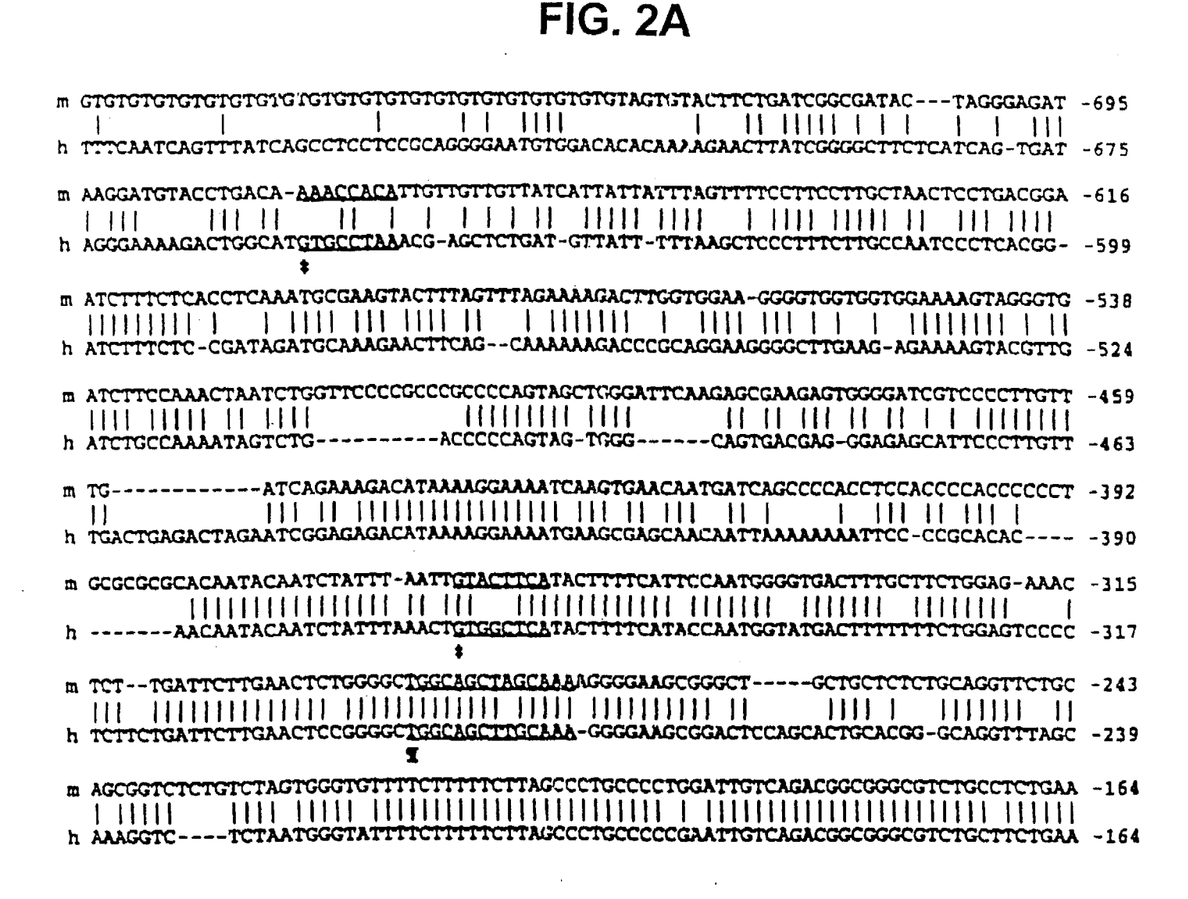
FIG. 2: Partial sequence of the promoter region of the murine (M) (SEQ ID No. 1) and the human (H) (SEQ ID No. 2) preproendothelin-1 gene. Identical sequence is indicated by vertical lines. The transcription start site is numbered 1. The CAAT and TATA consensus sequences are underlined bold. The GATA-2 binding site, the TPA/AP-1 binding sites, and the NF-1 binding element are indicated by the symbols *,‡, and ¶, respectively. The BglII site in the non-coding area of the first exon is marked. The preproendothelin-1 ATG is indicated in bold and the first intron in lower case letters.
Figure 2B:
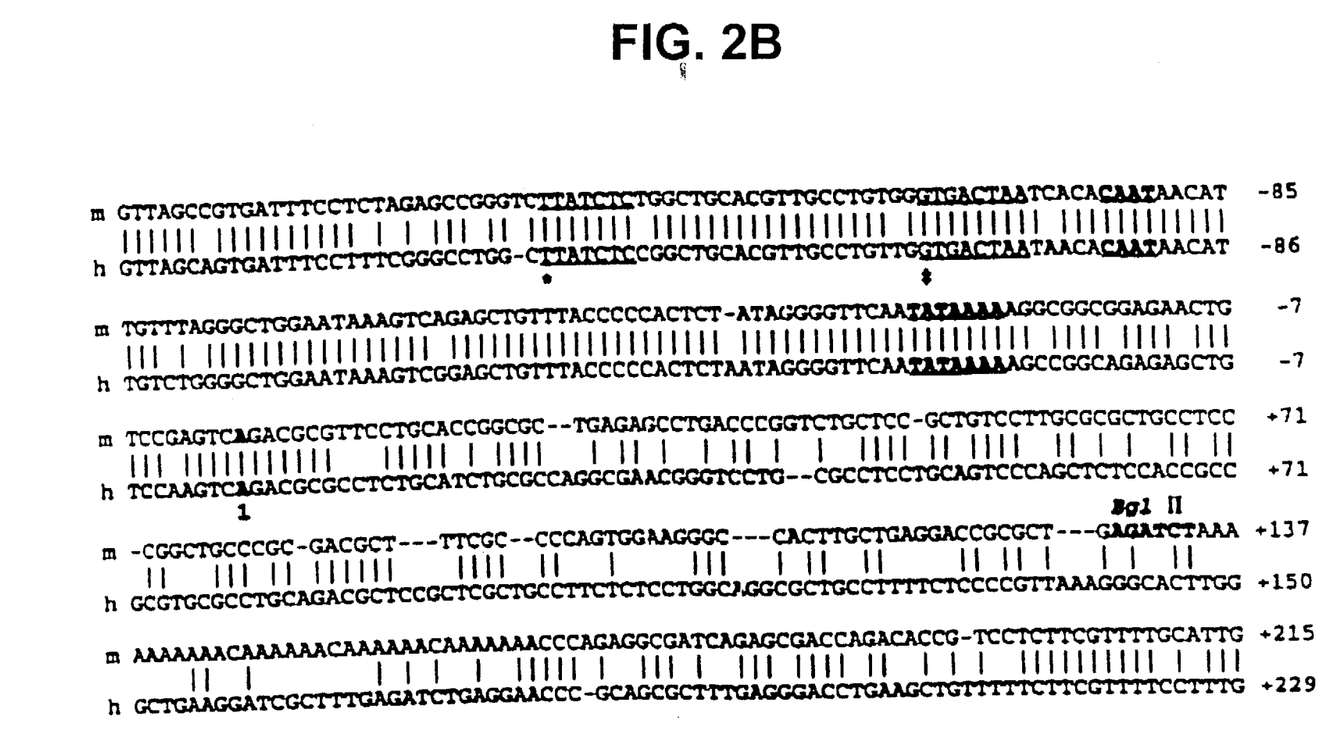
Figure 2C:
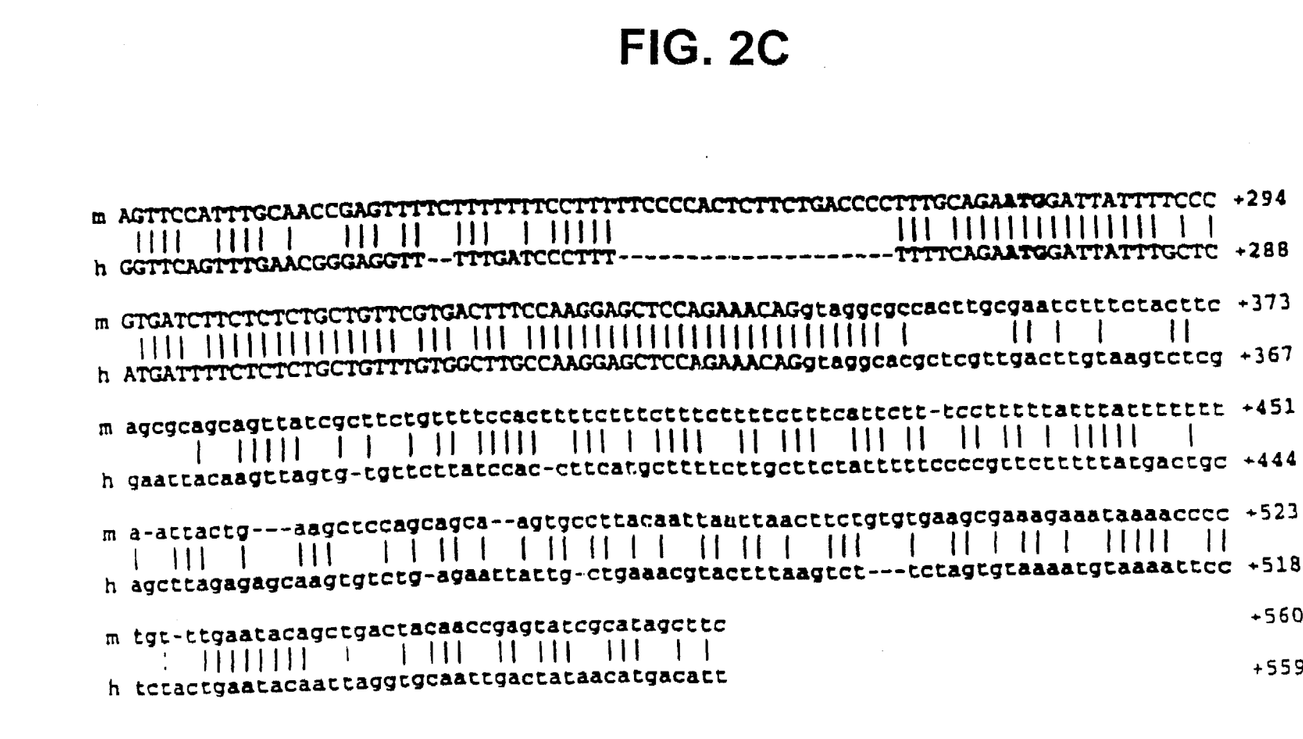

The genomic DNA sequence of the murine preproendothelin-1 (PPET-1) promoter region was determined (FIG. 2, SEQ ID No. 1). A clone containing the endothelin-1 coding region (exon 2) and more than 10 kb of the 5'-flanking promoter region was obtained. The genomic clone was verified by sequencing exon 2 which encodes the mature ET-1 peptide. This exon sequence was identical to the known murine cDNA sequence. Sequencing of 1057 bp of the 5'-flanking region, the first exon, and 200 bp of the first intrion of the murine gene revealed 67% identity to the human preproendothelin promoter (SEQ ID No. 2).

In FIG. 2 the transcription start site is numbered 1. The CAAT and TATA consensus sequences are underlined bold. The GATA-2 binding site, the TPA/AP-1 binding sites, and the NF-1 binding element are indicated by the symbols *,‡, and ¶, respectively. The BglII site in the non-coding area of the first exon is marked. The preproendothelin-1 ATG is indicated in bold and the first intron in lower case letters. The transcription start site, the CAAT and TATA consensus sequences, the GATA-2 binding site, and the AP-1 binding site were identical both in sequence and in location in the murine and the human PPET-1 gene.

EXAMPLE 2

Preproendothelin fusion gene plasmids

Fusion plasmids with firefly luciferase as a reporter gene were constructed by subcloning an EcoR I digest of the murine PPET-1 genomic fragment including 2.4 kb of the 5'-flanking region, the first exon of the gene and 0.8 kb of the first intron into pBluescript (Stratagene, La Jolla, Calif.). From this subclone a BamH I digest was excised including 1.4 kb of the 5'-flanking region, the first exon of the gene and 0.8 Kb of the first intron and subcloned into another pBluescript (p1.4PPET-Blu). Then a BamH I digest of the pGL-basic vector (Promega, Madison Wis.) containing the luciferase gene with its own ATG and stop codon as well as the SV40 intron/polyA signal was cloned into the noncoding region of the first exon (Bgl II site) in the p1.4PPET-Blu plasmid. This plasmid (called p1.4mPPET-LUC) was used for in vitro studies. From this new plasmid a BamH I-BamH I fragment with 1.4 kb of the 5'-flanking region, the first exon of the gene with the luciferase gene cloned into its Bgl II site, and 0.8 kb of the first intron was excised and placed downstream to a 4.5 kb Hind m-BamH I fragment from −5.9 to −1.4 kb of the murine PPET-1 5'-flanking region to create the final plasmid containing 5.9 kb of the 5'-flanking region (p5.9mPPET-LUC). Another reporter plasmid containing 0.45 kb of the 5'-flanking promoter region were constructed in a similar fashion (p0.45mPPET-LUC).

Figure 3:
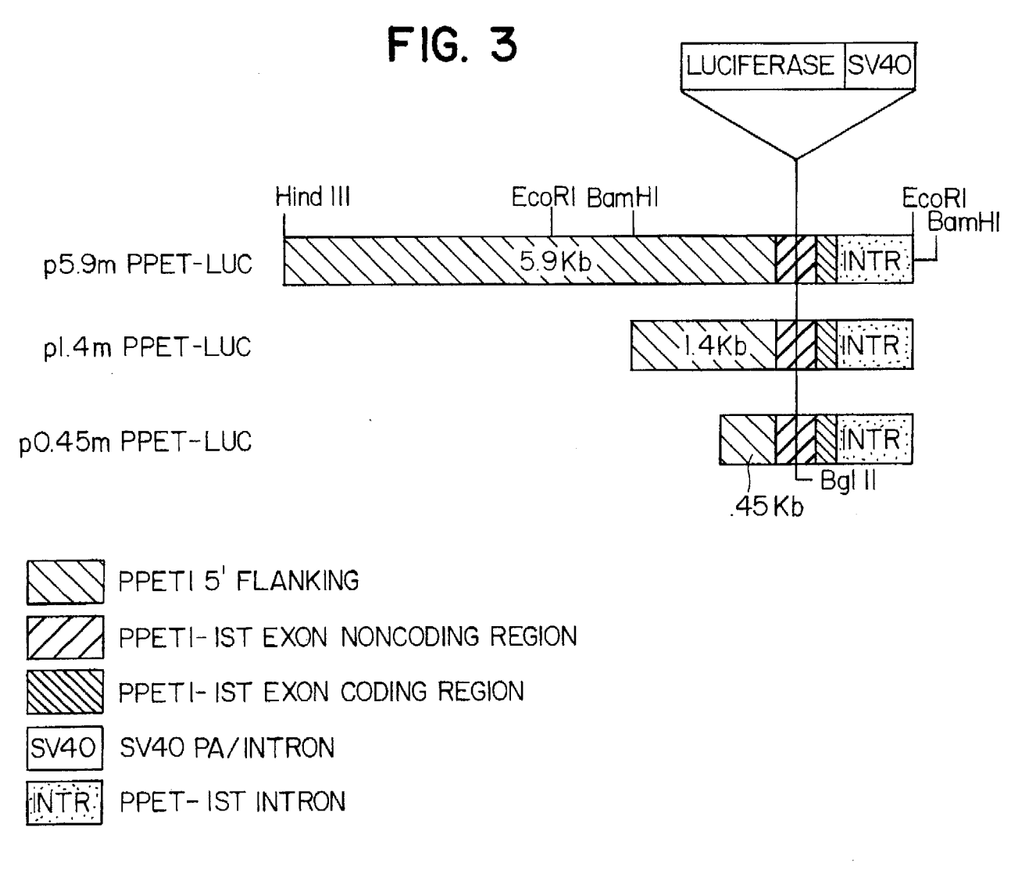
FIG. 3: Reporter fusion plasmids containing the 5'-flanking segment of variable length (5.9, 1.4 and 0.45 kb), the noncoding (hatched) and the coding (shaded) regions of the first exon and 0.8 kb of the first intron (INTR) of the mouse preproendothelin-1 gene.

As shown in FIG. 3, each plasmid contains a 5'-flanking region of variable length (5.9, 1.4, and 0.45 kb), the non-coding (hatched) and coding (shaded) regions of the first exon and 0.8 kb of the first intron (INTR) of the mouse preproendothelin-1 gene. The firefly luciferase gene with the SV40 intron/polyA signal was inserted at the BgM site of the first exon.

EXAMPLE 3

Cell specific expression of fusion gene plasmids

The plasmids of Example 2 were transfected into endothelial and non-endothelial cell lines and luciferase activity measured. To assess endothelial cell specificity, the endothelial and non-endothelial cell lines were transfected with either the PPET-LUC plasmids or with the SV40 minimal promoter-luciferase plasmid (pGL2-control vector; Promega, Madison Wis.).

Human umbilical vein endothelial cells (HUVEC) and the bovine pulmonary artery endothelial cell line, CPAE (ATCC, Rockville, Md.) were grown on human fibronectin-coated flasks (Biomedical Technologies Inc., Stoughton, Mass.) in Dulbecco modified Eagle medium supplemented with 20% fetal calf serum, 150 µg per ml endothelial cell growth supplement (Collaborative Research Inc. Bedford Mass.), 0.1 U of heparin per ml, 25 mM HEPES (N-2-hydroxyethylpiperazine-N'-2-ethanesulfonic acid), 1 mM sodium pyruvate, 1 mM non-essential amino acids solution, 50 U of penicillin per ml, 50µg of streptomycin per ml, and 2 mM glutamine. The murine fibroblast cell line, NIH 3T3 and the monkey kidney cell line, COS-7, were grown in Dulbecco modified Eagle medium supplemented with 10% fetal calf serum, 10 mM HEPES, 50 U of penicillin per ml, 50 µg of streptomycin per ml, and 2 mM glutamine. All cells were plated in 60 mm dishes at least 24 h before transfection. DNA transfection of HUVEC, CPAE, NIH 3T3, and COS-7 cells were performed with lipofectin reagent (Gibco, Grand Island, N.Y.) using standard techniques as described by Felgner et al., *Proc. Nat. Acad. Sci. USA*, 84:7413–7417 (1987), the disclosure of which is incorporated by reference herein. The cells (approximately 60% confluent) were transfected with 6 µg of the PPET-1 luciferase fusion gene plasmids (with 5.9, 1.4, and 0.45 kb 5'-flanking segments) or with the SV40 minimal promoter-luciferase plasmid (pGL2-control vector; Promega, Madison Wis.). The vector pSVβgalactosidase (4 µg) (Promega, Madison Wis.) was used as an internal standard for the transfection efficiency. A, plasmid with the 5.9 kb 5'-flanking region of the PPET-1 promoter and the luciferase gene in the reverse orientation was used as negative control. The cells were harvested 60 h after transfection and were assayed for luciferase and β-galactosidase activity.

The cells were washed and 250 µl of lysis buffer (Promega, Madison, Wis.) was added for 15 min. Cell lysates were then microcentrifuged (16,000 rpm × 1 min), and 20 µl of the clear supernatants were added to 100 µl of luciferase assay buffer (Promega, Madison, Wis.). The activity was measured in a Lumat LB 9501 Luminometer (Berthold, Gaithersburg, Md.) over a 20 second period. To assess luciferase activity, tissue (15 mg) was excised and homogenized in 1 ml of 15 mM $KH_2PO_4$ pH 7.5, 1 mM EDTA, 1 mM dithiothreitol, and 10% glycerol. To this homogenate 250 µl of 5× lysis buffer was added (Promega, Madison, Wis.) and the solution was shaken well for 15 min at room temperature. The solution was then centrifuged (13,000× g, 15 min) and 20 µl of the supernatant was assayed in the same manner as for the cells. Non-transgenic mice organs were processed in the same way and used as control. Results were expressed as luciferase light units per 1 µg of protein per 20 seconds. Protein was measured using the Bradford assay (Bradford, *Anal. Biochem.*, 72:248–254 (1976)) with bovine serum albumin (BSA) as a standard.

Figure 4:
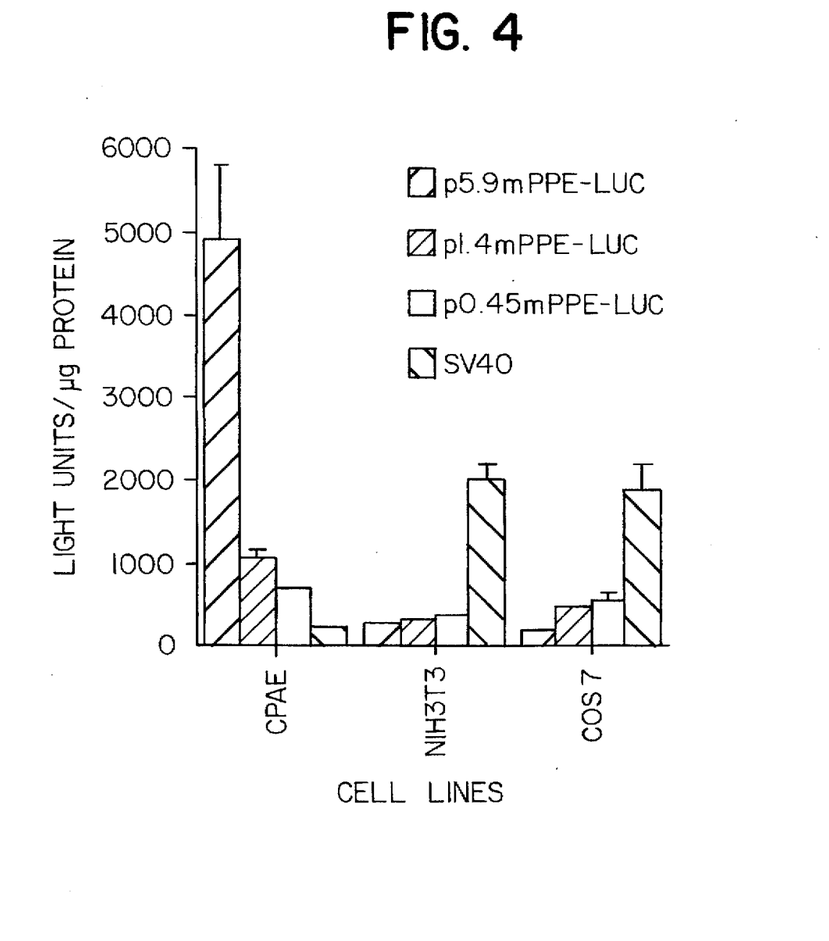
FIG. 4: Cell-specific expression of the murine preproendothelin-1 gene in vitro. The results represent the means and standard deviations of five independent transfections. Reading from left to right, there are three cell lines: bovine pulmonary artery endothelial cells (CPAE), murine fibroblast cells (NIH-3T3), and monkey kidney cells (COS-7). Each cell line was transfected with the four vectors (p5.9mPPE-LUC, p1.4mPPE-LUC, p0.45mPPE-LUC, and control SV40). Only in CPAE was there significant expression of the LUC vectors.

The ratio of the luciferase activity obtained with the preproendothelin versus the SV40 promoter was calculated in each cell line to account for the variability of transfection tendency of the different cell lines. All three PPET-1 constructs showed endothelial cell specificity with the most cell-specific construct being the p5.9mPPET-LUC. Five independent transfections were conducted and the mean and one standard deviation are shown in FIG. 4. All three constructs exhibited tissue specific expression. The p5.9mPPET-LUC plasmid yielded 5 to 7 times more luciferase activity in transfecting the bovine pulmonary artery endothelial cell line (CPAE) than the plasmids containing the 1.4 or the 0.45 kb regions, respectively. In human endothelial cells EEC) p5.9mPPET-LUC gave 2–3 times more luciferase activity than the plasmids containing the 1.4 or 0.45 kb regions.

EXAMPLE 4

Generation of transgenic mice

The 5.9 kb PPET-1 5'-flanking promoter region—luciferase expression cassette (5.9PPET-LUC) was liberated from the p5.9PPET-LUC by Xho I and Not I digestion, purified by agarose gel electrophoresis and Geneclean kit (Bio 101, Mount Prospect, Ill.). Purified DNA (1–2 μg per ml) was redissolved in 5 mM Tris, pH 7.4, 0.1 mM EDTA prior to pronuclear injection. Donor eggs were prepared from C57B6/SJL F1 mice obtained from Jackson Laboratory (Bar Harbor, Me.). Microinjected eggs were then transferred into to the oviducts of CD-1 foster mothers (Charles River Breeding Laboratories, Wilmington, Mass.) to create the reporter transgenic mice, tg5.9mPPET-LUC. PPET1-15LO transgenic mice were created using similar techniques. Founders were screened by polymerase chain reaction using primers to the 3' end of the PPET-1 promoter sequence and the 5' end of the 15-lipoxygenase cDNA.

Of the 160 live-born offspring of the tg5.9mPPET-LUC, twenty-nine were founders as determined by luciferase activity in tail extracts and confirmed by Southern blot analysis of tail DNA using a 360-bp luciferase gene sequence as probe. Of these founders, 16 had more than 100 light units per μg protein of tail extract (Table 1). Five independent founders with high levels of luciferase activity in tails were crossbred for several generations with wild type C57B6/SJL mice to establish heterozygote colonies tg5.9mPPET-LUC 1 to 5, with the highest level of expression in colony 2 and the lowest in colony 1.

Figure 5A:
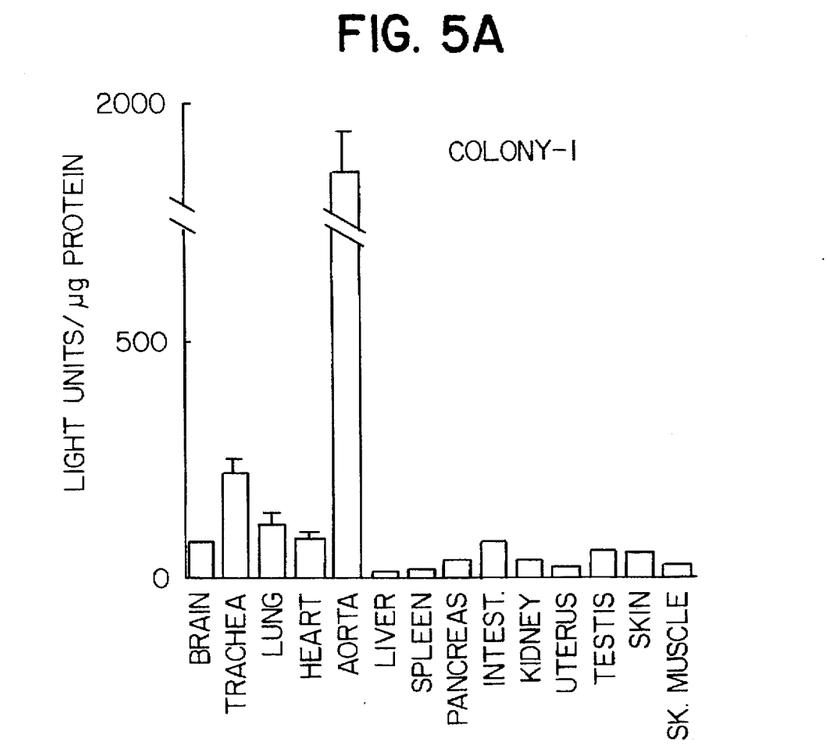
FIG. 5: Tissue luciferase activity in two transgenic colonies derived from independent founders. The mean and standard deviation of luciferase activity in light units per microgram protein are shown for mice from the lowest and highest activity colonies.
Figure 5B:
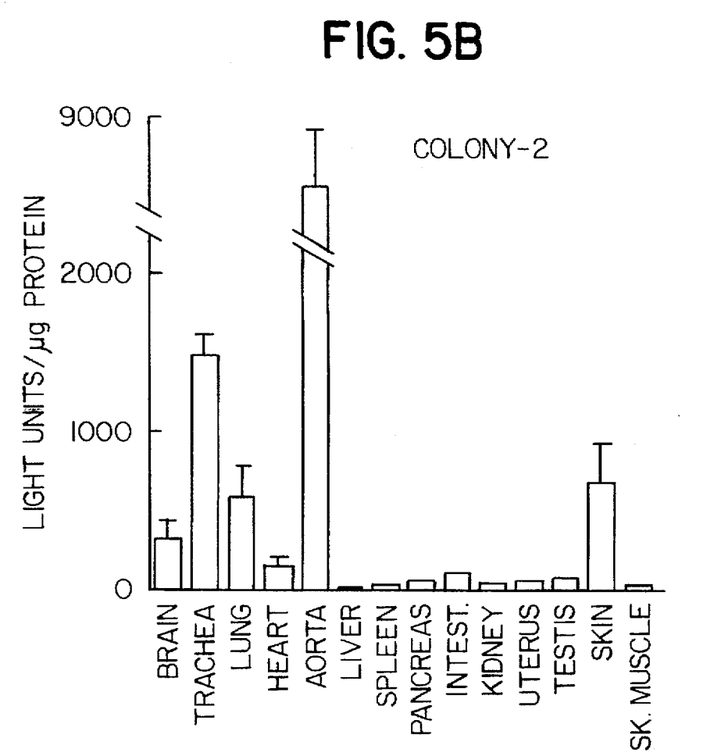

To study the tissue distribution of the luciferase gene directed by the murine PPET-1 promoter, 21 transgenic mice from the five colonies established from independent founders and 8 non-transgenic mice were sacrificed at the age of 3 months. Luciferase activity was measured in different organs. In all transgenic mice, the highest level of expression was ill the aorta. Although the different colonies showed different levels of luciferase expression, the tissue distribution was identical as shown for the lowest and the highest expressing colonies in FIG. 5.

TABLE 1

Luciferase expression in tails of 3 week old mice from different generations (F0, F1 and F2.

| Luciferase Activity (Light units/μg Protein) | | Number Of Mice Analyzed | | |
|---|---|---|---|---|
| | | F0 | F1 | F2 |
| | | 160 | 202 | 50 |
| Low activity | ($10-10^2$) | 13 | 16 | 2 |
| Medium activity | ($10^2-10^3$) | 12 | 55 | 27 |
| High activity | ($10^3-10^4$) | 4 | 24 | 5 |
| Total Positives | | 29 | 95 | 34 |

Results represent number of animals in each group.

The most significant expression of luciferase was in the aorta and the vasculature throughout the body but some organs showed more vascular expression than others. Even in the same organ some arteries showed high expression, while others showed little or no expression. In addition, expression was often in the intima and media of large muscular arteries, but only in endothelial cells in other vessels. In non-vascular cells the most significant expression was in the respiratory epithelium, which cells are known to express ET-1 although at a lower level than endothelial cells. The pattern of vascular and non-vascular expression of luciferase in the transgenic mice is generally consistent with the previously described distribution of ET-1 in mammals.

EXAMPLE 6

Isolation of aonic vessel wall cells

Mouse aortic endothelial and non-endothelial cells were obtained from five transgenic (tg5.9mPPE-LUC) and five non-transgenic mice. Aortas were surgically dissected, rinsed in ice cold phosphate buffered saline (PBS), minced to one by one mm and digested in an enzyme mixture containing DME/F12, 0.5% BSA, 0.2% Collagenase, 6 U/ml Dispase (Collaborative Research, Bedford, Mass.), and 10 μg/ml DNase (Boehringer Mannheim, Indianapolis, Ind.). The endothelial and smooth muscle cells were then separated over a Nycodenze gradient and affinity purified over lectin magnetic beads as taught in P. Belloni. et al., Microvasc. Res. 43:20–45 (1992), the disclosure of which is incorporated by reference herein. The two fractions were then stained with anti-Von Willebrand antibody to identify endothelial cells (DAKO, Carpinteira, Calif.).

The "endothelial" fraction had 90% endothelial cells and the "non-endothelial" fraction had <10% endothelial cells, as determined by endothelial specific staining with anti-Von Willebrand antibody (data not shown). The luciferase activity was 4.3 times higher in the "endothelial" than in the "non-endothelial" cell fraction (41,750 and 9,673 light units/ $2 \times 10^5$ cells respectively).

EXAMPLE 7

Immunohistochemistry

To determine the tissue distribution and cellular localization of luciferase expression, primary organs were prepared for immunofluorescence analysis by freezing in OCT immediately after necropsy. Serial sections (10 μm) were fixed briefly in acetone at −20° c. Sections were then immersed sequentially in PBS containing 0.5%BSA and 10% normal goat sera (blocking solution) (10 min), followed by blocking solution containing 10 μg/ml avidin (10 min), blocking solution containing 10 μg/ml biotin (10 min), and primary rabbit anti-luciferase antisera 1:500/blocking solution (90 min). Anti-luciferase antisera was generated by immunizing rabbits with luciferase (Sigma, St Louis, Mo.) using, in sequence, Freund's complete and incomplete adjuvant and aluminum adjuvant (Pierce, Rockford, Ill.). The resulting anti-luciferase serum detected 0.5 ng luciferase on immunoblots (1:100 dilution) and detected luciferase expression in appropriate transfected cell lines. Bound primary antibody was detected by incubation with biotinylated goat-anti-rabbit IgG (1:250) (Vector Labs, Burlingame, Calif.) followed by streptavidin-FITC (1:200) (Pierce, Rockford, Ill.). Immunofluorescence was detected on a Axiovert Microscope (Leica Inc., Deerfield, Ill.). Sections were counterstained with propidium iodide (Sigma, St Louis, Mo.) to identify cellular architecture. Anti-Von Willebrand antibody or anti-smooth muscle-actin antibody (DAKO, Carpinteira, Calif.) were used to identify endothelial cells or smooth muscle cells, respectively. Transgenic tissue stained with preimmune sera and non-transgenic tissue stained with the luciferase antisera were used to assess non-specific fluorescence.

Immunoperoxidase staining was assessed on 5 μm sections prepared from formalin-fixed paraffin embedded tissues. Sections were deparaffinized, and permeabilized with PBS containing 0.2% Nonident-P40 detergent (Sigma, St. Louis, Mo.). Sections were then immersed sequentially in PBS containing 0.5% BSA and 10% normal goat sera (blocking solution) (10 min), followed by blocking solution containing 10μg/ml biotin (10 min), and primary rabbit anti-luciferase antisera 1:500/blocking solution (overnight at 4° C.). The sections were then incubated with biotinvlated goat-anti-rabbit IgG (1:250) (Vector Labs, Burlingame, Calif.), and endogenous peroxidase activity. was then quenched with 3% $H_2O_2$ for 5 min. Bound primary antibody was detected by ABC (Vector Labs, Burlingame, Calif.) followed by the substrate, aminoethylcarbazole (AEC, Vector Labs, Burlingame, Calif.) or diaminobenzadine (DAB, Vector Labs, Burlingame, Calif.), and counterstained with hematoxylin. Transgenic tissue stained with preimmune sera and non-transgenic tissue stained with the luciferase antisera were used to assess non-specific staining.

Immunohistochemical staining of the aorta showed high levels of luciferase expression in the aortic wall but not in the surrounding tissue as shown by nuclear staining with propidium iodide. Endothelial-specific staining with anti-Von Willebrand antibody, and smooth muscle cell-specific staining with anti-actin antibody indicate that the luciferase expression was in the intima (endothelial cells), the media (smooth muscle cells), as well as the vasa vasorum. Staining of the aorta from 5.9 PPET-LUC transgenic mice with preimmune serum, and the aorta of PPET-15LO transgenic control mice with anti-luciferase anti-sera were both negative. High levels of expression were also noted in other large arteries, in small muscular arteries, and to a lesser extent in capillaries throughout the body. Lower levels of expression were noted in veins. Some organs such as the heart, kidney, and lung showed more vascular expression than others. The liver and the spleen showed minimal vascular expression. Even in the same organ some arteries showed high levels of expression while others showed little or none. In large, muscular arteries the expression was in the intima and media, but in small arteries, veins and capillaries the expression was confirmed to the endothelial cells.

In most organs the expression was confirmed to the vascular tissue, but in others some non-vascular expression was detected as shown in the kidney and the lung. The most significant non-vascular expression was detected in the airway epithelium as shown by luciferase activity in the trachea and by anti-luciferase staining of the lung. Similar expression was detected in salivary gland epithelium. The glomeruli showed high levels of expression both in the endothelial and the mesangial cells. The epithelium of the small intestine showed expression that increased gradually from the basal cells (no expression) toward the mature cells lining the lumen. Different regions of the brain showed different levels of luciferase expression, identical to the published distribution of endothelin in the brain, (Lee et al., *J. Clin. Invest.*, 86:141–149 (1990)). Other select non-vascular cells showed much lower levels of luciferase activity. This pattern of immunofluorescence staining was confirmed by peroxidase staining of paraffin sections.

EXAMPLE 8

Transgenic Mice Expressing Human 15-Lipoxygenase

The 5.9 kb 5'-flanking sequence of the murine preproendothelin-1 gene was used to express the human 15-lipoxygenase (15-LO) in transgenic mice as described in Examples 2 and 4, substituting the gene for 15-LO for the luciferase reporter gene. Two heterozygote colonies from independent founders were established. Mice from each colony were analyzed for the expression of the heterologous 15-lipoxygenase enzyme by immunocytochemistry using an anti-human 15-lipoxygenase antibody and showed 15-lipoxygenase expression in the vascular wall of various organs. To determine the tissue distribution and cellular localization of 15-lipoxygenase expression, primary organs were prepared as described above for the luciferase staining and stained with rabbit-anti human 15-lipoxygenase antibody as described in E. Sigal et al., *J. Bio. Chem.*, 265:5113–5120 (1990) and *Am. J. Physiol.* 262:L392-L398 (1992), the disclosures of which are incorporated by reference herein.

In non-vascular tissue, the highest expression was again observed in the airway epithelium. Other non-vascular tissues showed minimal or no expression. Non-transgenic mice stained with 15-lipoxygenase antibody showed no immunoreactivity. Transgenic mice stained with non-immune rabbit IgG showed no immunoreactivity.

EXAMPLE 9

Enzymatic Activity of 15-LO Transgenic Mice

Activity assays on various tissues confirmed that the human 15-lipoxygenase expressed in the transgenic mice was enzymatically active. The enzyme product, 15-hydroxyeicosatetraenoic acid (15-HETE) was measured by modification of the standard HPLC technique (Simon, et al., *Atherosclerosis* 75:31–38 (1989)). Transgenic and non-transgenic control mice were euthanaised and perfused with cold saline (left ventricle to right atrium). Organs were then harvested, trimmed from the fat and the connective tissue around them, weighed, minced and resuspended in one ml of cold PBS, 5 mM glucose, pH 7.4. About 200 mg tissue was used for each activity assay. In small organs such as the aorta (5 to 12 mg each) three mice were combined as one sample. The reactions were carried out in 1 ml at 37° C. for 15 min., using 20μM cold arachidonic acid and 2 μci $C^{14}$ arachidonic acid as a substrate for the lipoxygenase. The reaction was terminated with 100 μl glacial acetic acid and the lipids were extracted with one volume of isopropylalcohol and one volume of chloroform. An aliquot of prostaglandin $B_2$ was used as an internal standard. All extracts were dried under $N_2$ and stored at −70° C. Extracts were reconstituted in chromatography solvent and were analyzed by reverse-phase HPLC on a Shimadzu CR4-A chromatography system using Adsorbosil C18 column (5 μm, 4.6 mm×25 cm, Alltec). The column was developed at a flow rate of 1.0 ml/min by a gradient program using two solvents (A and B) set at 55% B for 0–16 min, 70% B for 17–37 min, 100% B from 38–56 min, and 55% B for 56–60 min. Solvent-A was methanol/water/acetic acid (50:50:0.01) and B was methanol/water/acetic acid (90:10:0.01). The HPLC eluate was monitored using a Shimadzu SPD-6AV detector set at 270 nm from 0–14 min to detect the prostaglandin $B_2$, 235 nm from 15–60 min to detect monoHETEs, and a Beckman 171 Radioisotope detector for radioactivity measurements. Products were quantitated using standard molar absorption coefficients and a known mixture of prostaglandin $B_2$, 5, 12, and 15-HETE, and $C^{14}$-15-HETE. In extracts of heart tissue from transgenic mice, 4.43±0.99 ng 15-HETE was detected per mg tissue (n=8). This was significantly different (p<0.01) from levels obtained from extracts of heart tissue of non-transgenic mice (0.026±0.03, n=5). In aortic tissues of transgenic mice 5.86±0.49 ng 15-HETE per mg tissue was detected. Aortas of non-transgenic mice contained no detectable 15-HETE production. 15-HETE was also detected in tracheas and brains of transgenic mice (3.56±1.18 and 0.27±0.06 ng/mg tissue res tissue respectively, n=5) but not in non-transgenic mice (0.11±0.005 and 0.005±0.002 ng/mg tissue respectively, n=3). Both differences were statistically significant ($p<0.05$ and $p<0.01$ respectively). No 15-HETE was detected in the livers of transgenic or non-transgenic mice. It is of interest that in the trachea the levels of 15-HETE (which is the product of the human 15-lipoxygenase) were up to 7 times higher than that of 12-HETE which is the product of the murine 12-lipoxygenase normally expressed in this organ.

These Examples demonstrate that the sequences and vectors of this invention can be used to direct significant in vivo gene expression to the vascular wall. Expression in select epithelial cells, particularly those of the airway also occurs. However, expression in most non-vascular tissues is low.

The foregoing Examples are presented for illustrative purposes only and should not be construed so as to impart any implied limitations on the scope of the claims. The following claims particularly point out and distinctly claim the subject matter which applicants regard as their invention and are entitled to their full range of legal equivalents.

We claim:

1. A vector for expression of a nucleic acid casette comprising a murine preproendothelin-1 gene 5'-flanking segment, the first exon of the preproendothelin-1 gene, and a nucleic acid cassette, wherein the nucleic acid cassette is located within the first exon, in sequential and positional relationship for expression of the nucleic acid cassette.

2. A vector of claim 1 further comprising the first intron of the preproendothelin-1 gene, said intron located downstream from the first exon.

3. A vector of claim 2 comprising about 0.8 kb of the first intron.

4. A vector of claim 3 wherein the nucleic acid cassette is positioned between the noncoding and coding regions of said exon, in sequential and positional relationship for expression of the nucleic acid cassette.

5. A vector of claim 1 wherein the segment of the 5'-flanking region comprises about the first 0.45 kb upstream from the transcription start site.

6. A vector of claim 1 wherein the segment of the 5'-flanking region comprises about the first 1.4 kb upstream from the transcription start site.

7. A vector of claim 1 wherein the segment of the 5'-flanking region comprises about the first 5.9 kb upstream from the transcription start site.

8. A vector of claim 1 wherein the segment of the 5'-flanking region comprises about the first 9.1 kb upstream from the transcription start site.

9. A vector of claim 3 comprising 0.45 kb of the 5'-flanking region, the first exon, and about 0.8 kb of the first intron of the preproendothelin-1 gene.

10. A vector of claim 3 comprising 1.4 kb of the 5'-flanking region, the first exon, and about 0.8 kb of the first intron of the preproendothelin-1 gene.

11. A vector of claim 3 comprising 5.9 kb of the 5'-flanking region, the first exon, and about 0.8 kb of the first intron of the preproendothelin-1 gene.

12. A vector of claim 1 wherein the cassette comprises a nucleic acid sequence encoding a protein, a polypeptide, a ribozyme, or an antisense RNA.

13. The isolated genomic murine preproendothelin-1 5'-flanking region.

14. A plasmid comprising the 5'-flanking region of claim 13.

15. A method for expressing a gene of interest in vascular endothelial or bronchial epithelial cells which method comprises transfecting the cells with a vector of claim 1.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 1334 base pairs
    ( B ) TYPE: nucleic acid
    ( C ) STRANDEDNESS: single
    ( D ) TOPOLOGY: linear   ( i i ) MOLECULE TYPE: cDNA   ( i i i ) HYPOTHETICAL: NO   ( i v ) ANTI-SENSE: NO   ( x i ) SEQUENCE DESCRIPTION: SEQ ID NO:1:

```
GTGTGTGTGT   GTGTGTGTGT   GTGTGTGTGT   GTGTGTGTGT   GTGTAGTGTA   CTTCTGATCG        60
GCGATACTAG   GGAGATAAGG   ATGTACCTGA   CAAAACCACA   TTGTTGTTGT   TATCATTATT       120
ATTTAGTTTT   CCTTCCTTGC   TAACTCCTGA   CGGAATCTTT   CTCACCTCAA   ATGCGAAGTA       180
CTTTAGTTTA   GAAAAGACTT   GGTGGAAGGG   GTGGTGGTGG   AAAAGTAGGG   TGATCTTCCA       240
AACTAATCTG   GTTCCCCGCC   CGCCCCAGTA   GCTGGGATTC   AAGAGCGAAG   AGTGGGGATC       300
GTCCCCTTGT   TTGATCAGAA   AGACATAAAA   GGAAAATCAA   GTGAACAATG   ATCAGCCCCA       360
CCTCCACCCC   ACCCCCCTGC   GCGCGCACAA   TACAATCTAT   TTAATTGTAC   TTCATACTTT       420
TCATTCCAAT   GGGGTGACTT   TGCTTCTGGA   GAAACTCTTG   ATTCTTGAAC   TCTGGGGCTG       480
GCAGCTAGCA   AAAGGGGAAG   CGGGCTGCTG   CTCTCTGCAG   GTTCTGCAGC   GGTCTCTGTC       540
TAGTGGGTGT   TTTCTTTTTC   TTAGCCCTGC   CCCTGGATTG   TCAGACGGCG   GGCGTCTGCC       600
TCTGAAGTTA   GCCGTGATTT   CCTCTAGAGC   CGGGTCTTAT   CTCTGGCTGC   ACGTTGCCTG       660
TGGGTGACTA   ATCACACAAT   AACATTGTTT   AGGGCTGGAA   TAAAGTCAGA   GCTGTTTACC       720
CCCACTCTAT   AGGGGTTCAA   TATAAAAAGG   CGGCGGAGAA   CTGTCCGAGT   CAGACGCGTT       780
CCTGCACCGG   CGCTGAGAGC   CTGACCCGGT   CTGCTCCGCT   GTCCTTGCGC   GCTGCCTCCC       840
GGCTGCCCGC   GACGCTTTCG   CCCCAGTGGA   AGGGCCACTT   GCTGAGGACC   GCGCTGAGAT       900
CTAAAAAAAA   AACAAAAAAC   AAAAAACAAA   AAACCCAGA   GGCGATCAGA   GCGACCAGAC       960
ACCGTCCTCT   TCGTTTTGCA   TTGAGTTCCA   TTTGCAACCG   AGTTTCTTT   TTTCCTTTT       1020
TCCCCACTCT   TCTGACCCCT   TTGCAGAATG   GATTATTTTC   CCGTGATCTT   CTCTCTGCTG      1080
TTCGTGACTT   TCCAAGGAGC   TCCAGAAACA   GGTAGGCGCC   ACTTGCGAAT   CTTTCTACTT      1140
CAGCGCAGCA   GTTATCGCTT   CTGTTTTCCA   CTTTCTTTC   TTTCTTTTCT   TTCATTCTTT      1200
```

-continued

| | | | | | |
|---|---|---|---|---|---|
| CCTTTTTATT | TATTTTTTA | ATTACTGAAG | CTCCAGCAGC | AAGTGCCTTA | CAATTAATTA | 1260 |
| ACTTCTGTGT | GAAGCGAAAG | AAATAAAACC | CCTGTTTGAA | TACAGCTGAC | TACAACCGAG | 1320 |
| TATCGCATAG | CTTC | | | | | 1334 |

( 2 ) INFORMATION FOR SEQ ID NO:2:

( i ) SEQUENCE CHARACTERISTICS:
        ( A ) LENGTH: 1308 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( x i ) SEQUENCE DESCRIPTION: SEQ ID NO:2:

| | | | | | |
|---|---|---|---|---|---|
| TTTCAATCAG | TTTATCAGCC | TCCTCCGCAG | GGGAATGTGG | ACACACAAAA | GAACTTATCG | 60 |
| GGGCTTCTCA | TCAGTGATAG | GGAAAAGACT | GGCATGTGCC | TAAACGAGCT | CTGATGTTAT | 120 |
| TTTTAAGCTC | CCTTTCTTGC | CAATCCCTCA | CGGATCTTTC | TCCGATAGAT | GCAAAGAACT | 180 |
| TCAGCAAAAA | AGACCCGCAG | GAAGGGGCTT | GAAGAGAAAA | GTACGTTGAT | CTGCCAAAAT | 240 |
| AGTCTGACCC | CCAGTAGTGG | GCAGTGACGA | GGGAGAGCAT | TCCCTTGTTT | GACTGAGACT | 300 |
| AGAATCGGAG | AGACATAAAA | GGAAAATGAA | GCGAGCAACA | ATTAAAAAAA | ATTCCCCGCA | 360 |
| CACAACAATA | CAATCTATTT | AAACTGTGGC | TCATACTTTT | CATACCAATG | GTATGACTTT | 420 |
| TTTTCTGGAG | TCCCTCTTC | TGATTCTTGA | ACTCCGGGGC | TGGCAGCTTG | CAAAGGGGAA | 480 |
| GCGGACTCCA | GCACTGCACG | GGCAGGTTTA | GCAAAGGTCT | CTAATGGGTA | TTTTCTTTTT | 540 |
| CTTAGCCCTG | CCCCCGAATT | GTCAGACGGC | GGGCGTCTGC | TTCTGAAGTT | AGCAGTGATT | 600 |
| TCCTTTCGGG | CCTGGCTTAT | CTCCGGCTGC | ACGTTGCCTG | TTGGTGACTA | ATAACACAAT | 660 |
| AACATTGTCT | GGGGCTGGAA | TAAAGTCGGA | GCTGTTTACC | CCCACTCTAA | TAGGGGTTCA | 720 |
| ATATAAAAAG | CCGGCAGAGA | GCTGTCCAAG | TCAGACGCGC | CTCTGCATCT | GCGCCAGGCG | 780 |
| AACGGGTCCT | GCGCCTCCTG | CAGTCCCAGC | TCTCCACCGC | CGCGTGCGCC | TGCAGACGCT | 840 |
| CCGCTCGCTG | CCTTCTCTCC | TGGCAGGCGC | TGCCTTTTCT | CCCCGTTAAA | GGGCACTTGG | 900 |
| GCTGAAGGAT | CGCTTTGAGA | TCTGAGGAAC | CCGCAGCGCT | TGAGGGACC | TGAAGCTGTT | 960 |
| TTTCTTCGTT | TTCCTTTGGG | TTCAGTTTGA | ACGGGAGGTT | TTTGATCCCT | TTTTTTCAGA | 1020 |
| ATGGATTATT | TGCTCATGAT | TTTCTCTCTG | CTGTTTGTGG | CTTGCCAAGG | AGCTCCAGAA | 1080 |
| ACAGGTAGGC | ACGCTCGTTG | ACTTGTAAGT | CTCGGAATTA | CAAGTTAGTG | TGTTCTTATC | 1140 |
| CACCTTCATG | CTTTTCTTGC | TTCTATTTTT | CCCCGTTCTT | TTTATGACTG | CAGCTTAGAG | 1200 |
| AGCAAGTGTC | TGAGAATTAT | TGCTGAAACG | TACTTTAAGT | CTTCTAGTGT | AAAATGTAAA | 1260 |
| ATTCCTCTAC | TGAATACAAT | TAGGTGCAAT | TGACTATAAC | ATGACATT | | 1308 |